Figure 1:
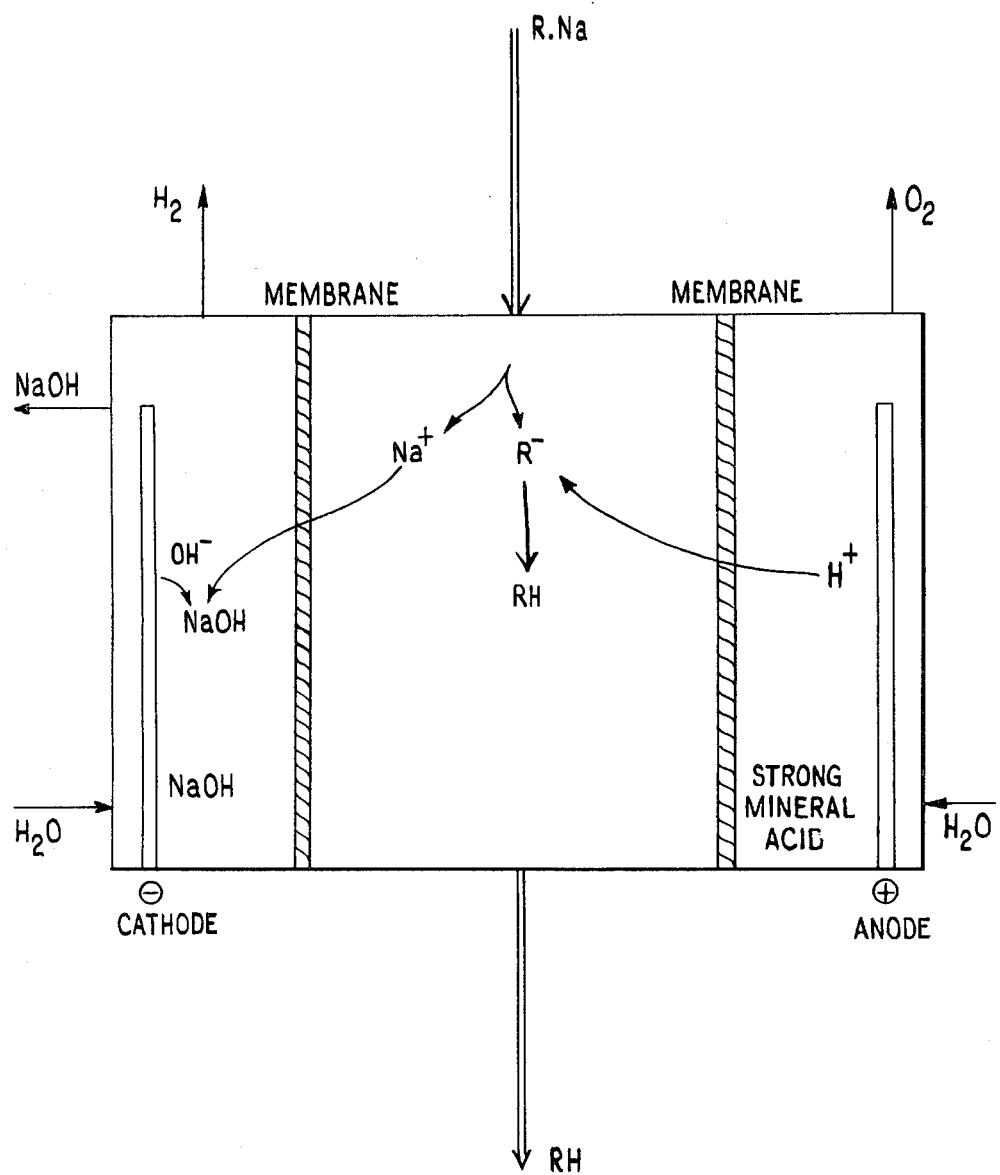

United States Patent [19]

Bachot et al.

[11] 4,454,012

[45] Jun. 12, 1984

[54] PROCESS FOR THE PREPARATION OF METHIONINE

[75] Inventors: Jean Bachot, Fontenay-aux-Roses; Jean Grosbois, L'Isle-Adam, both of France

[73] Assignee: Rhone-Poulenc Industries, Paris, France

[21] Appl. No.: 487,075

[22] Filed: Apr. 21, 1983

Related U.S. Application Data

[63] Continuation of Ser. No. 234,498, Feb. 17, 1981, abandoned.

[30] Foreign Application Priority Data

Feb. 19, 1980 [FR] France .................................. 80 03581

[51] Int. Cl.³ .......................... C25B 3/00; C25B 7/00
[52] U.S. Cl. ................................... 204/72; 204/180 P
[58] Field of Search ................... 204/59 R, 72, 180 P

[56] References Cited

U.S. PATENT DOCUMENTS 2,921,005  1/1960  Bodamer .............................. 204/72
4,092,230  5/1978  Norton ........................... 204/180 P Primary Examiner—F. Edmundson
Attorney, Agent, or Firm—Stevens, Davis, Miller & Mosher

[57] ABSTRACT

Crystalline methionine is prepared from an alkali metal methioninate by continuously electrolyzing an aqueous solution of the said alkali metal methioninate and a support electrolyte in an intermediate compartment of a cell comprising an anode compartment, an intermediate compartment containing the said aqueous solution and separated from the anode compartment by a cationic membrane, and a cathode compartment separated from the intermediate compartment by a cationic membrane, so that the alkali metal ions of the said methioninate are replaced by hydrogen ions generated in the anode compartment and themselves migrate to the cathode compartment to form an alkali metal hydroxide therein, and recovering free crystalline methionine from the electrolyzed aqueous solution in the said intermediate compartment, and alkali metal hydroxide from the said cathode compartment.

3 Claims, 3 Drawing Figures $R = CH_3 S\ CH_2\ CH_2 - \underset{\underset{NH_2}{|}}{CH} - COO$ $$R = CH_3 S\ CH_2\ CH_2-CH-COO$$
$$\underset{NH_2}{|}$$

PROCESS FOR THE PREPARATION OF METHIONINE

This is a continuation of application Ser. No. 234,498 filed Feb. 17, 1981, now abandoned.

The present invention relates to a process for the preparation of crystalline methionine from an aqueous solution essentially containing an alkali metal methioninate.

It is known to prepare methionine by displacement from one of its salts, such as an alkali metal salt or alkaline earth metal salt, using a strong mineral acid, such as sulphuric acid or hydrochloric acid. The use of a process of this type usually results in the co-production of a mineral salt, such as sodium sulphate, which is difficult to utilize or market.

Furthermore, it is known, in particular from French Pat. No. 75/04,380 (2,260,558) and U.S. Pat. No. 3,330,749, to prepare organic acids, such as citric acid or aminoacids, by electrolytic processes. However, in these processes, it is necessary to recycle the solutions of unhydrolysed salts many times, or the processes cannot be carried out continuously.

The present invention provides a continuous process for the preparation of methionine in the crystalline form from an alkali metal methioninate which comprises electrolysing an aqueous solution of the said alkali metal methioninate and a support electrolyte in an intermediate compartment of a cell comprising an anode compartment, an intermediate compartment, containing the said aqueous solution and separated from the anode compartment by a cationic membrane, and a cathode compartment separated from an intermediate compartment by a cationic membrane, so that the alkali metal ions of the said methioninate are replaced by hydrogen ions generated in the anode compartment and themselves migrate to the cathode compartment to form an alkali metal hydroxide therein, and recovering free crystalline methionine from the electrolysed aqueous solution in the said intermediate compartment, and alkali metal hydroxide from said cathode compartment. In this process a solution of an alkali metal methioninate and a support electrolyte, which may be a carbonate of the same alkali metal, is subjected, in an electrolysis-/electrodialysis cell, to a sufficient potential difference, and, in the intermediate compartment, the alkali metal ions from the methioninate are replaced by hydrogen ions originating from the anode compartment. Free methionine in crystalline form and alkali metal hydroxide regenerated in the cathode compartment are isolated.

In the anode compartment, separated from the intermediate compartment by a membrane referred to as an "anodic" membrane, the water is oxidised according to the reaction:

In the cathode compartment, separated from the intermediate compartment by a membrane referred to as a "cathodic" membrane, the water is reduced according to the reaction:

The protons (H+) formed during the oxidation reaction pass through the anodic membrane by electromigration and displace methionine from the salt contained in the intermediate compartment.

Simultaneously, the alkali metal ions released pass through the cathodic membrane and combine in the cathode compartment with the hydroxyl ions to give the corresponding alkali metal hydroxide.

The methionine is separated from the solution from the intermediate compartment by appropriate methods, e.g. by filtering off the crystals which form after cooling.

The anolyte contained in the anode compartment preferably consists of an aqueous solution of a strong mineral acid. The anion of the strong mineral acid must be such that it is electrochemically inert. Sulphuric acid or nitric acid is particularly suitable for this purpose. The concentration of acid in the anode compartment is generally between 1 and 4N and preferably between 1 and 2N, depending on the characteristics of the electrodes.

However, it is possible for the concentration of acid to be lower, and it can be as low as 0.1N if this improves the operation of the electrode. The loss of water due to the electrolysis is compensated by the continuous addition of water to the cell.

The catholyte preferably consists of a solution of an alkali metal hydroxide, the concentration of which is generally between 2 and 14N and preferably between 6 and 12N. The concentration essentially depends on the quality of the membrane. The alkali metal hydroxide formed is drawn off continuously and its concentration in the cell is kept constant by the continuous addition of water.

In the intermediate compartment, the width of which is generally between 1 and 3 cm but can be less, i.e. of the order of 0.5 cm, there is an aqueous solution of an alkali metal salt of methionine containing a supporting electrolyte. The supporting electrolyte can be a highly dissociated mineral salt which is very soluble in the medium and which has a high conductivity, a carbonate of the same alkali metal or a mixture thereof. The supporting electrolyte must also be chosen so that its presence does not hinder the subsequent separation of the crystalline methionine.

The displacement of the methionine in the intermediate compartment generally takes place at a pH which is as close as possible to that of its isoelectric point or neutralization point. The pH is generally between 2 and 6 and preferably of the order of 4 when the support electrolyte contains a strongly dissociated mineral salt. The pH can be controlled automatically and/or by adding a salt which can buffer the medium, such as sodium acetate or sodium phosphate.

When the support electrolyte contains only an alkali metal carbonate, it is particularly advantageous to operate at a higher pH, so that there is only partial displacement from the alkali metal salt in question, i.e. at a pH of between 6 and 10 and more particularly between 8 and 9.

If the anolyte consists of sulphuric acid, the anode generally consists of a titanium plate covered with lead dioxide or with electroplated platinum, or of a titanium plate covered with a precious metal, precious metal oxide or manganese oxide. Preferably, the anode is made of titanium covered with electroplated platinum. Advantageously, a platinum grid can also be used.

The cathode is generally made of nickel or soft iron, which may be covered with a coating of catalyst to increase the active surface or reduce the hydrogen over-voltage.

The membranes must possess certain characteristics. More particularly, they must be cationic, resistant to the medium and highly conducting.

The anodic membrane must have a cation transport number which is as close as possible to 1, and it must be impermeable to the anion.

The cathodic membrane must only transport cations which are common to the hydroxide produced at the cathode, and it must have high performance, i.e. it must resist the transport of hydroxyl ions in the reverse direction.

The ion-exchange resins which can be used to manufacture the membranes are sulphonic acid cation-exchange resins and carboxylic acid cation-exchange resins. In the first of these, the ion-exchange groups are hydrated sulphonic acid radicals ($SO_3H.xH_2O$), and in the second of these, the ion-exchange groups are carboxylic acid groups (COOH). The membranes made of sulphonated polymer are particularly suitable. Amongst the latter, the membranes of perfluorocarbonsulphonic acids ensure excellent transport of cations, are very stable, are not attacked by acids and strong oxidising agents and possess excellent heat stability. The membranes marketed by the Société Du Pont de Nemours under the trademark NAFION are particularly suitable, e.g. Nafion 110 and 117 which are made of a fluorinated polymer containing sulphonic acid groups and Nafion 214 and 215 which are made of fluorinated polymers containing sulphonic acid groups and which have one face (the anodic face) treated with an amine.

The voltage at the terminals of the cell is generally between 4 and 10 volts, taking account of the overvoltage of each of the two electrodes, the resistance of the ion-exchange membranes and the secondary reactions which can take place at the electrodes, and the distance separating the electrodes.

It is desirable to operate at high current densities, which are generally of the order of 25 to 30 $A/dm^2$, and this requires fewer cells and lower investment costs.

It is particularly advantageous to operate at a temperature between 75° and 95° C. and preferably of the order of 90° C.

FIG. 1 is a construction diagram of the cell, in which the methionine is initially in the form of the sodium salt.

By way of example, a process for the preparation of methionine from 3-methylthiopropionaldehyde by a chemical method can be represented schematically as follows:

$$CH_3SCH_2CH_2CHO + NaCN + NH_3 + CO_2 \longrightarrow$$

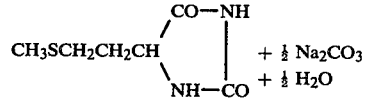
$+ \frac{1}{2} Na_2CO_3$
$+ \frac{1}{2} H_2O$

-continued

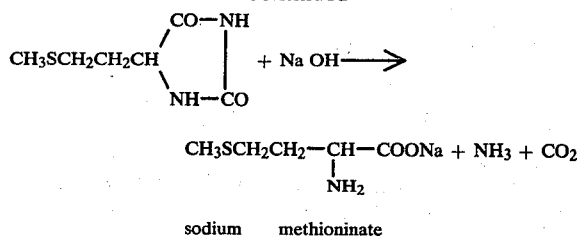
$+ NaOH \longrightarrow$ $$CH_3SCH_2CH_2-\underset{\underset{NH_2}{|}}{CH}-COONa + NH_3 + CO_2$$

sodium methioninate

Other processes use potassium hydroxide in place of the sodium hydroxide or pass via an aminonitrile intermediate.

Using a chemical method, methionine can be displaced from its sodium or potassium salt by the action of sulphuric acid on the reaction medium, which contains sodium carbonate or potassium carbonate in addition to the sodium methioninate or potassium methioninate.

Using the electrolytic process described above, it is possible, for example, to displace methionine from its sodium or potassium salt whilst avoiding the production of sodium sulphate or potassium sulphate. As the sodium hydroxide or potassium hydroxide is regenerated in the cathode compartment, it can be re-used for the hydrolysis of the hydantoin or the aminonitrile.

Furthermore, if the intermediate compartment is fed with a solution containing a mixture of alkali metal methioninate and carbonate, the carbon dioxide produced in the intermediate compartment can be recovered and re-used in carrying out the chemical process.

In the electrolysis/electrodialysis cell, the anode compartment contains a solution of a strong acid, such as sulphuric acid or nitric acid, the concentration of which is generally between 2 and 5N but can have a lower limit of 0.1N, and it is fed with water;

the cathode compartment contains an aqueous solution of sodium hydroxide or potassium hydroxide, which becomes progressively richer in sodium hydroxide pr potassium hydroxide. When the concentration of sodium hydroxide or potassium hydroxide reaches the desired level (from 2 to 14N), the solution of alkali metal hydroxide is drawn off and the cell is fed with water at the same rate, so as to keep the concentration constant within the cathode compartment; and the intermediate compartment is fed with a solution of sodium methioninate or potassium methioninate, containing sodium carbonate or potassium carbonate. The supporting electrolyte can also consist of an alkali metal sulphate or nitrate. The displacement of the carbon dioxide from the sodium carbonate or potassium carbonate and the displacement of the methionine from its salt take place simultaneously. As the presence of carbon dioxide in the cell is disadvantageous (it increases the voltage because of the resistance of the bubbles), the displacement can be carried out in a part of the intermediate compartment through which the electric current substantially does not pass, the hydrogen ions being transferred into a part of the intermediate compartment which is independent of the electrolyser and which contains the solution of the alkali metal methioninate and alkali metal carbonate. It will be understood in this connection that the part of the intermediate compartment through which the electric current does not pass may be a separate vessel fed continuously or intermittently from the main part of the intermediate compartment forming part of the cell.

The anode, the cathode and the membranes used are of the type described above.

The voltage at the terminals of the cell is generally of the order of 6 volts and the current density is of the order of 25 A/dm$^2$.

The temperature inside the electrolyser is of the order of 80° C.

The separation of the methionine from the compartment in which it is displaced from its salt is carried out in accordance with the conventional methods. The methionine precipitates from its solution and is filtered off. Certain known additives for facilitating crystallisation, such as alcohols, phenols, soluble derivatives of cellulose, and the like, can be added. The filtrate, which contains the electrolyte, is recycled into the intermediate compartment.

Figure 2:
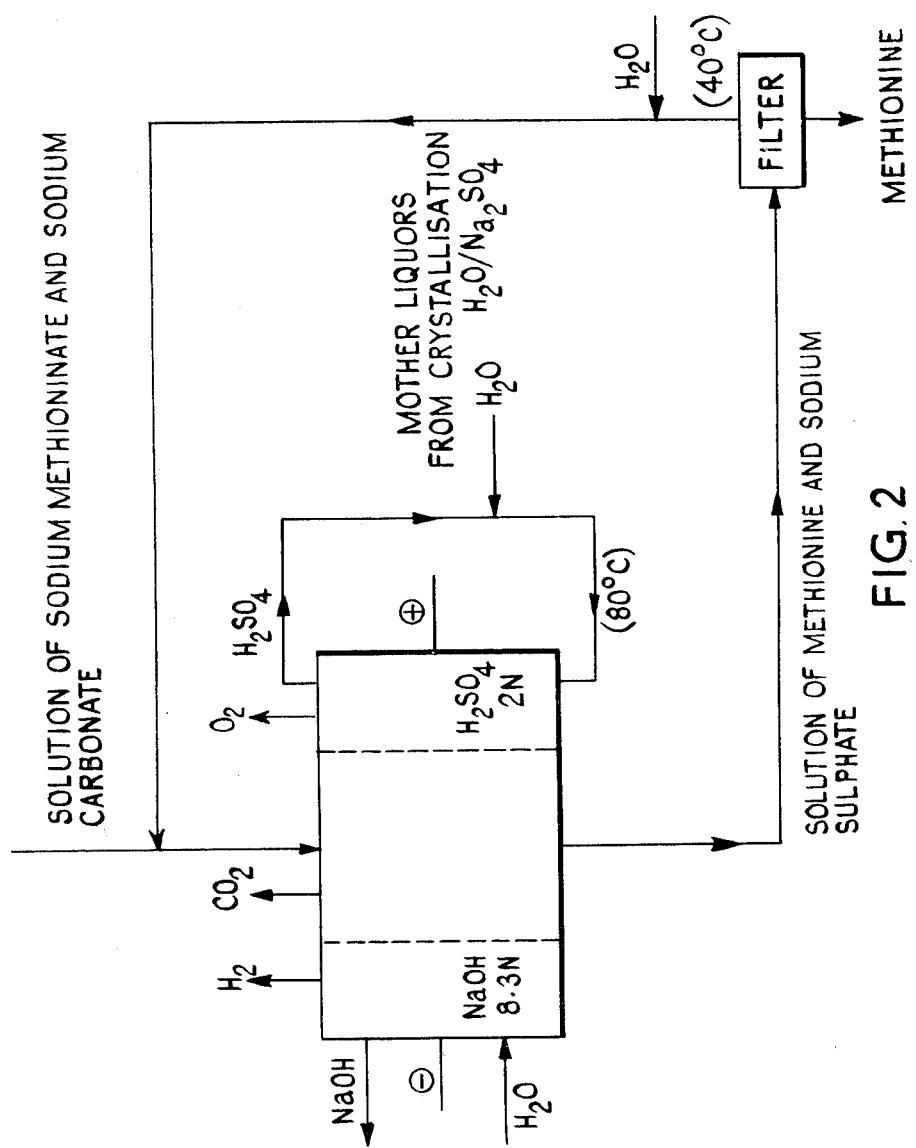
Figure 3:
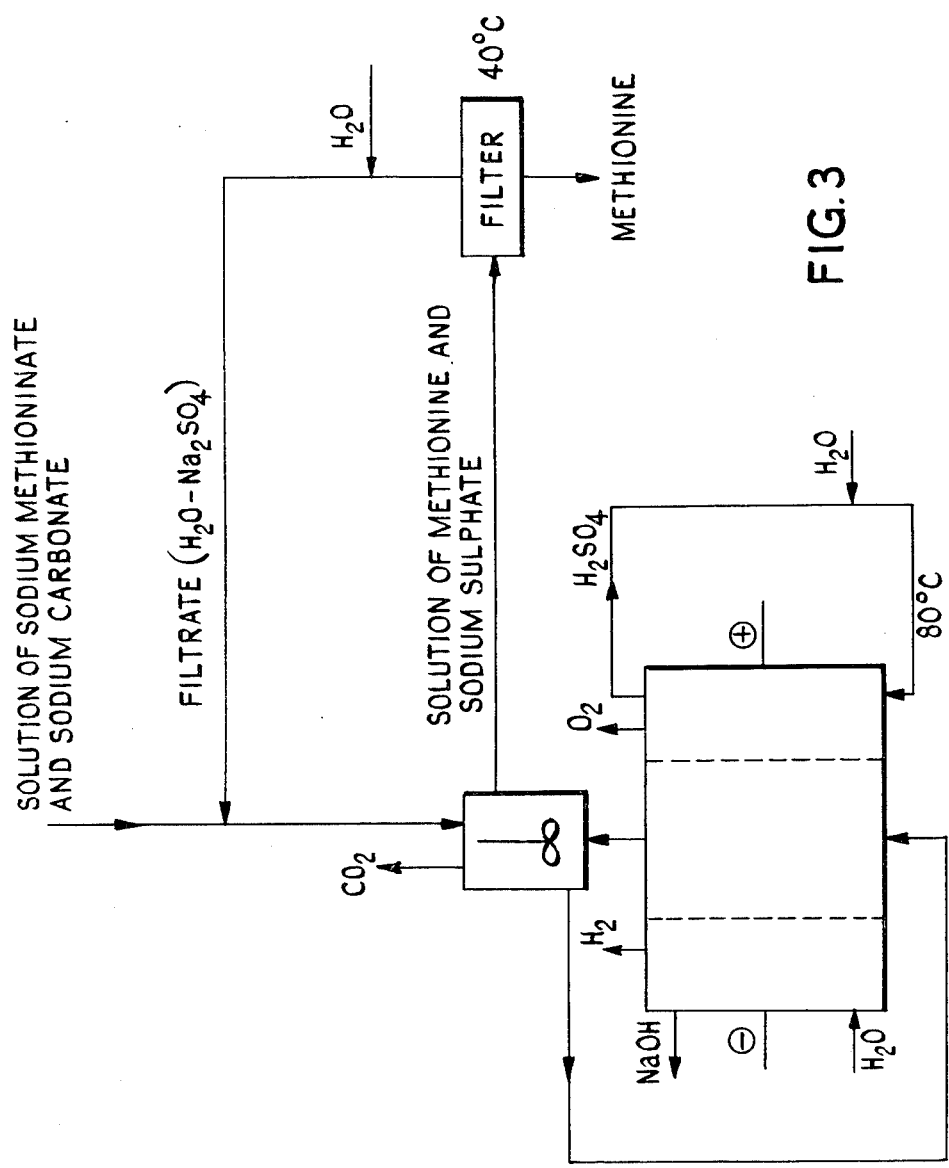

FIG. 2 gives the operation diagram of the cell for the isolation of the methionine, and FIG. 3 gives the operation diagram for the case where the methionine is displaced in a part of the intermediate compartment which is independent of the electrolyser.

The following Examples illustrate how the process of the invention is carried out.

EXAMPLE 1

The cell comprises three compartments separated by sulphonic acid membranes marketed by the Société Du Pont de Nemours under the trademark NAFION. The membrane separating the intermediate compartment from the anode compartment is a NAFION 110 membrane and that separating the intermediate compartment from the cathode compartment is a NAFION 215 membrane.

The anode consists of a 1 m$^2$ grid made of expanded metal (titanium) covered with lead oxide (PbO$_2$) and the cathode consists of a grid of the same surface area, made of Ghent steel (i.e. soft steel filaments interwoven and laminated) covered with a coating of an electrocatalyst based on titanium and nickel.

The anolyte consists of a 2N solution of sulphuric acid.

The cathode compartment is fed with water in such a way that the concentration of sodium hydroxide formed at the cathode reaches about 26% by weight.

The intermediate compartment, having a width of 26 mm, is fed with a solution of sodium methioninate and sodium carbonate and with a solution of sodium sulphate (in such a way that the concentration of sodium sulphate in the mixture is 2 M), the latter solution being intended to increase the electrical conductivity of the mixture. (The solution of sodium sulphate originates from the subsequent separation of the methionine).

The flow rate of the solution of sodium methioninate and sodium carbonate (which contains about 1 mol/liter of sodium methioninate and 0.85 mol/liter of sodium carbonate) is of the order of 30 liters/hour and depends on the pH of the intermediate compartment, which is adjusted to about 5. (This pH corresponds to the quantitative formation of methionine and carbon dioxide).

With the cell operating under a current density of 25 A/dm$^2$, the voltage set up is between 6.5 and 7 volts.

When operating under these conditions, the production of methionine is of the order of 4.5 kg/hour and that of sodium hydroxide is 13 kg/hour (26% by weight solution). The faradic efficiency is of the order of 90%.

The mixture originating from the intermediate compartment is then drawn off and the methionine is separated from the sodium sulphate by the usual processes, i.e. cooling to a temperature of the order of 40° C. and filtering off the crystalline methionine. The filtrate, which contains sodium sulphate, is recycled into the intermediate compartment.

EXAMPLE 2

The cell used is identical to that which is described in Example 1; in this cell, the NAFION 110 membrane is replaced by a NAFION 117 membrane and the intermediate compartment has a width of 13 mm, the anode, the cathode and the anolyte being the same as in Example 1 and the cathode compartment being fed with water in the same manner.

The intermediate compartment is fed with a solution of sodium methioninate and sodium carbonate and with a solution of sodium sulphate, in such a way that the concentration of sodium sulphate in the mixture is 1 M.

The flow rate of the solution of sodium methioninate and sodium carbonate (which contains about 1 mol/liter of sodium methioninate and 0.85 mol/liter of sodium carbonate) is of the order of 30 liters/hour and depends on the pH of the intermediate compartment, which is adjusted to about 5. Under these conditions, the actual concentration in the intermediate compartment is of the order 0.5 mol/liter of sodium methioninate and 0.43 mol/liter of sodium carbonate, taking account of the flow rate of the solution of sodium sulphate.

With the cell working under a current density of 25 A/dm$^2$, the voltage is 6.4 volts.

When operating under these conditions, the production of methionine is of the order of 4.5 kg/hour and that of sodium hydroxide is 13 kg/hour (as a 26% by weight solution). The faradic efficiency is of the order of 90%.

The methionine is isolated under the conditions described in Example 1.

EXAMPLE 3

The cell used is identical to that which is described in Example 1.

The anode consists of a 1 m$^2$ grid of expanded titanium covered with electrochemically deposited platinum (thickness: about 10μ) and the cathode consists of a grid of the same surface area, made of Ghent steel.

The anolyte consists of a 2N solution of nitric acid.

The cathode compartment is fed with water in such a way that the concentration of sodium hydroxide formed at the cathode reaches about 26% by weight.

The intermediate compartment, having a width of 26 mm, is fed with a solution of sodium methioninate and sodium carbonate, containing sodium nitrate (in an amount such that its concentration in the mixture is about 5N) in order to increase the electrical conductivity of the mixture.

The flow rate of the solution of sodium methioninate and sodium carbonate, which contains about 1 mol/liter of sodium methioninate and 0.85 mol/liter of sodium carbonate) is of the order of 30 liters/hour and depends on the pH of the intermediate compartment, which is adjusted to about 5.

With the cell working under a current density of 25 A/dm$^2$, the voltage is about 6 volts.

When operating under these conditions, the production of methionine is of the order of 4.5 kg/hour and that of sodium hydroxide is 13 kg/hour (as a 26% by weight solution). The faradic efficiency is of the order of 90%.

The methionine is isolated under the conditions described in Example 1.

EXAMPLE 4

The cell used is identical to that which is described in Example 1, except that the anode consists of a fine grid of platinum (220 g/m$^2$) and the intermediate compartment has a width of 13 mm.

The anolyte consists of a 2N solution of nitric acid.

The cathode compartment is fed with water in such a way that the concentration of sodium hydroxide formed at the cathode reaches about 26% by weight.

The intermediate compartment is fed with a solution of sodium methioninate and sodium carbonate and with a solution of sodium nitrate (in an amount such that the concentration of sodium nitrate in the mixture is about 3N).

The flow rate of the solution of sodium methioninate and sodium carbonate (which contains about 1 mol/liter of sodium methioninate and 0.85 mol/liter of sodium carbonate) is of the order of 30 liters/hour and varies according to the variation in the pH, which is initially adjusted to about 5.

With the cell working under a current density of 25 A/dm$^2$, the voltage is 5.5 volts.

When operating under these conditions, the production of methionine is of the order of 4.5 kg/hour and that of sodium hydroxide is 13 kg/hour (as a 26% by weight solution). The faradic efficiency is of the order of 90%.

The methionine is isolated under the conditions described in Example 1.

EXAMPLE 5

The cell used is identical to that which is described in Example 1. The anode consists of a 1 m$^2$ grid made of expanded metal (titanium) covered with lead oxide (PbO$_2$) and the cathode consists of a grid made of Ghent steel.

The anolyte consists of a 2N solution of sulphuric acid.

The cathode compartment is fed with water in such a way that the concentration of potassium hydroxide formed at the cathode reaches 26% by weight.

The intermediate compartment, having a width of 26 mm, is fed with a solution of potassium methioninate and potassium carbonate. A supporting electrolyte is not added.

The pH is fixed at a value which is such that the overall degree of conversion is about 50%, i.e. a value of between pH 10.2 and pH 6.4 and preferably of the order of 8.

In order to increase the stability of the potassium bicarbonate which ensures the passage of the current, and to delay its complete neutralisation, it is possible to operate under a slight pressure.

The flow rate of the solution of potassium methioninate and potassium carbonate is of the order of 30 liters/hour and depends on the pH of the intermediate compartment, which is adjusted to about 8.

With the cell working under a current density of 25 A/dm$^2$, the voltage is about 8.5 volts.

When operating under these conditions, the production of methionine is of the order of 4.5 kg/hour and that of potassium hydroxide is 18.0 kg/hour (as a 26% by weight solution). The faradic efficiency is of the order of 90%.

The methionine is isolated under the conditions described in Example 1.

EXAMPLE 6

The cell used is identical to that which is described in Example 1.

However, the cathodic membrane is a NAFION 214 membrane and the anode is a fine grid of platinum (220 g/m$^2$).

The anolyte consists of a 0.5N solution of sulphuric acid.

The cathode compartment is fed with water in such a way that the concentration of potassium hydroxide formed at the cathode reaches 26% by weight.

The intermediate compartment, having a width of 13 mm, is fed with a solution of potassium methioninate and potassium carbonate.

The pH is adjusted to 8.7; under these conditions, the degree of conversion is 53%.

The flow rate of the solution of potassium methioninate and potassium carbonate is adjusted according to the pH of the intermediate compartment.

With the cell working under a current density of 25 A/dm$^2$, the voltage is about 6.5 volts.

When operating under these conditions, the production of methionine is of the order of 4.5 kg/hour and that of potassium hydroxide is 18 kg/hour (as a 26% by weight solution). The faradic efficiency is of the order of 90%.

The methionine is isolated under the conditions described in Example 1.

EXAMPLE 7

The process is carried out under the conditions described in Example 6, the solution of potassium methioninate and potassium carbonate being replaced by a solution of sodium methioninate and sodium carbonate.

With the pH of the intermediate compartment adjusted to 8.4, the degree of conversion is of the order of 50%.

With the cell working under a current density of 25 A/dm$^2$, the voltage is about 7.1 volts.

When operating under these conditions, the production of methionine is of the order of 4.5 kg/hour and that of sodium hydroxide is 13 kg/hour (as a 26% by weight solution). The faradic efficiency is of the order of 90%.

The methionine is isolated under the conditions described in Example 1.

We claim:

1. Process for the continuous preparation of crystalline methionine from a solution containing an alkali metal methioninate and an alkali metal carbonate, which comprises:

continuously feeding an aqueous solution containing said alkali metal methioninate and either an alkali metal carbonate, or both an alkali metal carbonate and a support electrolyte which is a highly dissociated mineral salt which is very soluble in the medium and which has a high conductivity, to the intermediate compartment of a cell comprising an intermediate compartment and anode and cathode compartments each separated from said intermediate compartment by a cationic membrane;

electrolysing at 75° to 95° C. said aqueous solution, so that hydrogen ions generated in the anode compartment migrate to the intermediate compartment and, in a part of the intermediate compartment through which the electric current substantially does not pass, displace the alkali metal ions of said methioninate to form methionine and also convert the carbonate ions into carbon dioxide, and the alkali metal ions migrate from the intermediate compartment to the cathode compartment to form an alkali metal hydroxide therein;

continuously withdrawing electrolysed aqueous solution from said intermediate compartment; and cooling said electrolysed solution to cause methionine to crystallize out, and recovering the crystalline methionine so obtained, and also recovering alkali metal hydroxide from said cathode compartment.

2. Process according to claim 1 in which the supporting electrolyte is a mixture of alkali metal sulphate or nitrate and the alkali metal carbonate and the resultant electrolyzed solution withdrawn from the said intermediate compartment has a pH of between 2 and 6.

3. Process according to claim 1 in which the support electrolyte is the alkali metal carbonate and the electrolysed solution withdrawn from the said intermediate compartment has a pH of between 6 and 10.

* * * * *